United States Patent
Smith (10) Patent No.: US 9,408,739 B2
(45) Date of Patent: *Aug. 9, 2016

(54) PREFABRICATED WALKING BOOT

(71) Applicant: Joseph C. Smith, Sinking Spring, PA (US)

(72) Inventor: Joseph C. Smith, Sinking Spring, PA (US)

(*) Notice: Subject to any disclaimer, the term of this patent is extended or adjusted under 35 U.S.C. 154(b) by 231 days.

This patent is subject to a terminal disclaimer.

(21) Appl. No.: 14/013,800

(22) Filed: Aug. 29, 2013

(65) Prior Publication Data

US 2015/0065935 A1    Mar. 5, 2015

(51) Int. Cl.
*A61F 5/00* (2006.01)
*A61F 5/01* (2006.01)

(52) U.S. Cl.
CPC .................................... *A61F 5/0111* (2013.01)

(58) Field of Classification Search
CPC ... A61F 5/0111; A61F 5/0127; A61F 5/0102; A61F 5/0113; A61F 5/0125; A61F 2005/0179; A61F 13/067; A61F 2005/0139; A61F 5/012; A61F 5/14; A61F 2002/5003; A61F 2002/5072; A61F 2002/6621; A61F 5/0585; A61F 13/064; A61F 13/066; A61F 5/019; A61F 5/34; A61F 2/3859; A61F 2/389; A61F 2220/0041; A61F 2/4684; A61F 2220/0033; A61F 2002/30433; A61F 2002/30507; A61F 2002/4631; A61F 2220/0025; A61F 2310/00017; A43B 7/20; A43B 5/00; A43B 7/32; A43B 5/04; A43B 5/0427; A43B 7/01

USPC .............. 602/23–28, 60–62; 128/882; 5/624
See application file for complete search history.

(56) References Cited

U.S. PATENT DOCUMENTS

| | | | |
|---|---|---|---|
| 5,219,324 A * | 6/1993 | Hall | A61F 5/0111 602/27 |
| 6,945,947 B2 * | 9/2005 | Ingimundarson | A61F 5/0113 128/882 |
| 7,077,818 B2 * | 7/2006 | Ingimundarson | A61F 5/0113 128/882 |
| 7,988,654 B2 * | 8/2011 | Leatherwood-Maxwell | A61F 5/0111 128/882 |
| 8,480,604 B2 * | 7/2013 | Messer | A61F 5/0111 602/27 |

* cited by examiner

*Primary Examiner* — Michael Brown
(74) *Attorney, Agent, or Firm* — Duane Morris LLP (57) ABSTRACT

The present invention includes a walking boot device which immobilizes the ankle at about a 90° angle using a single anterior post that is angled at about 90° at an ankle joint from a lateral view, and encompasses an anterior one half of a calf proximally, and a dorsal one half of a forefoot distally. The post includes medial and lateral wings. The present invention defines an area for a medial and lateral malleolus and is narrow at the ankle and wider at the calf for a more anatomical fit. The present invention is secured to a leg using hook and loop fastener (Velcro®) strapping attached proximally around the calf posteriorly, away from any bony prominences. The hook and loop fastener (Velcro®) strapping is attached to the medial and lateral wings through brackets that are riveted into the wings. The present invention further includes foam inserts and a pneumatic bladder.

18 Claims, 11 Drawing Sheets

PREFABRICATED WALKING BOOT

FIELD OF THE INVENTION

The present invention relates generally to orthopedic and orthotic braces and supports, and more specifically to a prefabricated walking boot which serves as an ankle and foot brace or support.

BACKGROUND OF THE INVENTION

Orthopedic and orthotic braces and supports are used to immobilize lower extremities to allow for healing and avoiding further damage of the lower extremities. Ankle-foot orthosis (AFO), in particular, is used to treat numerous ailments that may affect an ankle and/or foot. One type of AFO is a cast walker or walking boot. A cast walker allows a patient to put weight on an injured area, unlike a non-walking cast which requires that the patient keep weight entirely off the injured area by relying on crutches to walk.

In current practice, walking boots are made with two straight posts that come up from a foot bed on either side of the ankle, directly over a medial and lateral malleolus. The malleolus is a bony prominence on each side of the ankle These posts run parallel from the ankle to a calf, not taking into account the difference in diameter from the ankle to the calf. Presently, most products limit motion using hook and loop fastener (Velcro®) straps.

Many times, the walking boot posts cause irritation to the medial and lateral ankle bones and calf area where the walking boot ends proximally. The hook and loop fastener (Velcro®) straps used in walking boots are often inadequate at limiting movement and also cause irritation over a shin. Additionally, current walking boots frequently create knee, hip, and back pain because of a height inequality when compared to shoe gear on an opposing limb.

The above-described irritation and pain of current walking boots frequently lead patients to refuse to wear walking boots or remove walking boots prematurely, which in turn, decreases patient compliance and delays healing.

SUMMARY OF THE INVENTION

The present invention includes a walking boot device which immobilizes an ankle at about a 90° angle using a single anterior post that is angled at about 90° at an ankle joint from a lateral view, and encompasses an anterior one half of a calf proximally, and a dorsal one half of a forefoot distally. The present invention defines an area for a medial and lateral malleolus and is narrow at the ankle and wider at the calf for a more anatomical fit. The present invention is secured to a leg using hook and loop fastener (Velcro®) strapping attached proximally around the calf posteriorly, away from any bony prominences.

A principal object of the invention is to provide an improved walking boot device.

Still another object of the invention is to provide an improved walking boot device that adequately limits the movement of the lower extremities while avoiding irritation of the medial and lateral ankle bones and calf area using a single anterior post that is angled at about 90° at the ankle joint from a lateral view, and encompasses the anterior one half of the calf proximally, and the dorsal one half of the forefoot distally.

Still another object of the invention is to provide an improved walking boot device that avoids irritation of the medial and lateral ankle bones and calf area by securing the device to the leg using hook and loop fastener (Velcro®) strapping attached proximally around the calf posteriorly, away from any bony prominences.

Still another object of the invention is to provide an improved walking boot device that takes into account the difference in diameter from the ankle to the calf by curving more narrowly at the ankle and more widely at the calf for a more anatomical fit.

Still another object of the invention is to provide an improved walking boot device that accommodates for height inequality of opposing shoe gear by being low-profile and having foam inserts of varying thickness.

These and other objects will be apparent to those skilled in the art.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein.

DETAILED DESCRIPTION OF THE INVENTION

The advantages of the present invention, as outlined above, are that it provides a more comfortable and accurate fit without irritation of the medial and lateral ankle bones and calf area, accommodates the varying height of opposing shoe gear, and adequately limits movement in the lower extremities while keeping the ankle joint at approximately a 90° angle.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," "bottom," "distal," "proximal," "dorsal," "plantar," "lateral," "medial," "anterior," and "posterior" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise.

In a preferred embodiment, the present invention relates to a walking boot device 2 which immobilizes an ankle 4 at about a 90° angle using a single anterior post 6 that is angled at about 90° at an ankle joint 8 from a lateral view, and encompasses an anterior one half of a calf 10 proximally, and a dorsal one half of a forefoot 12 distally, as illustrated in FIGS. 1-3, and 5-7.

Figure 1:
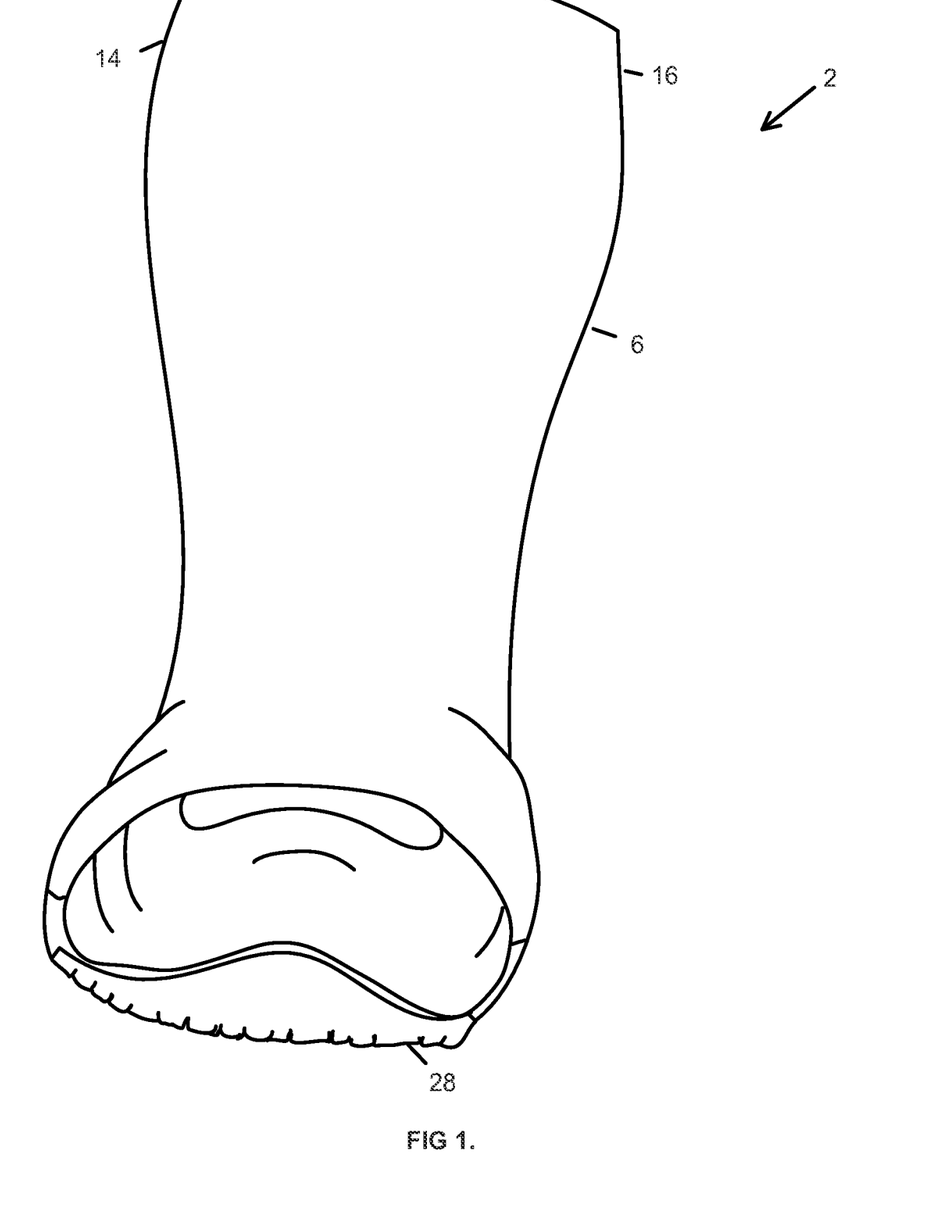
FIG. 1 is a front elevation view of one embodiment of a walking boot device in accordance with the present invention.
Figure 2:
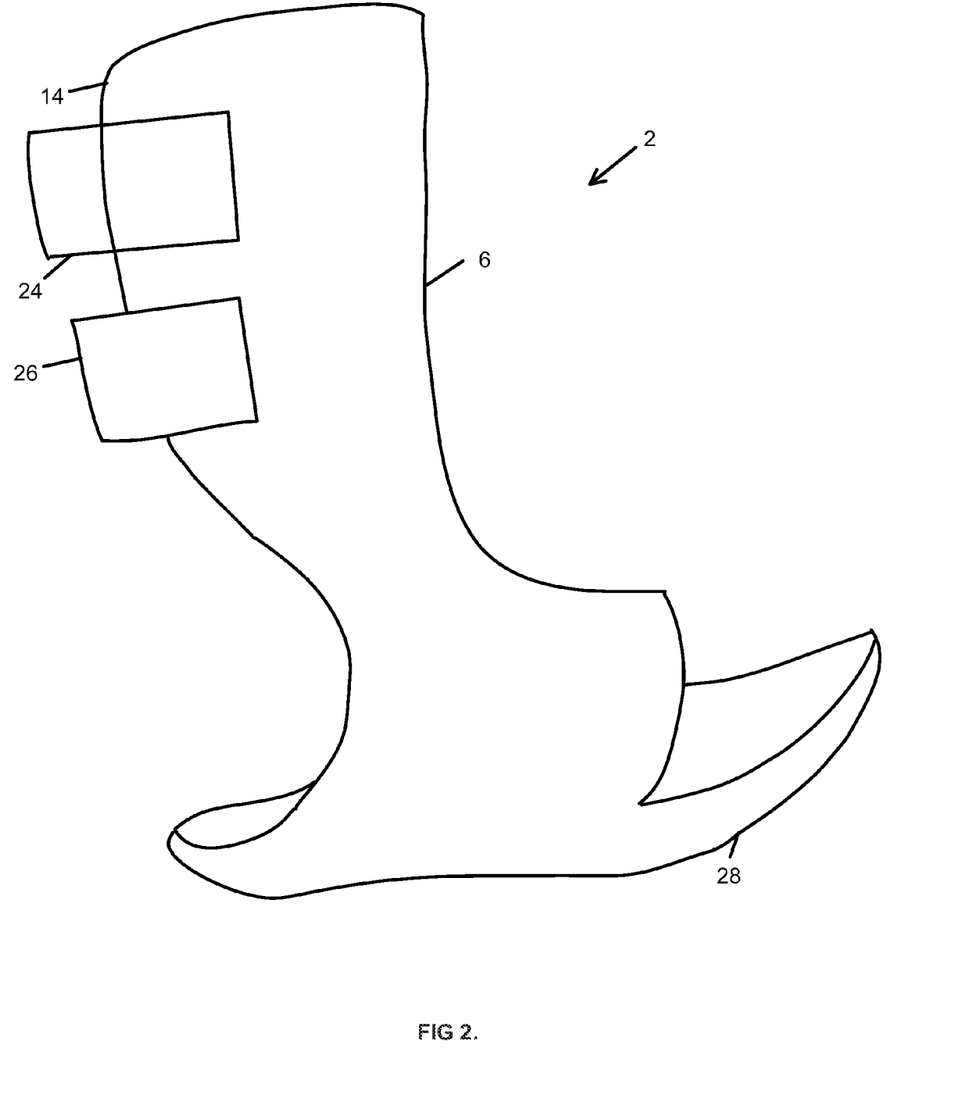
FIG. 2 is a side elevation view of one embodiment of the walking boot device in accordance with the present invention.
Figure 3:
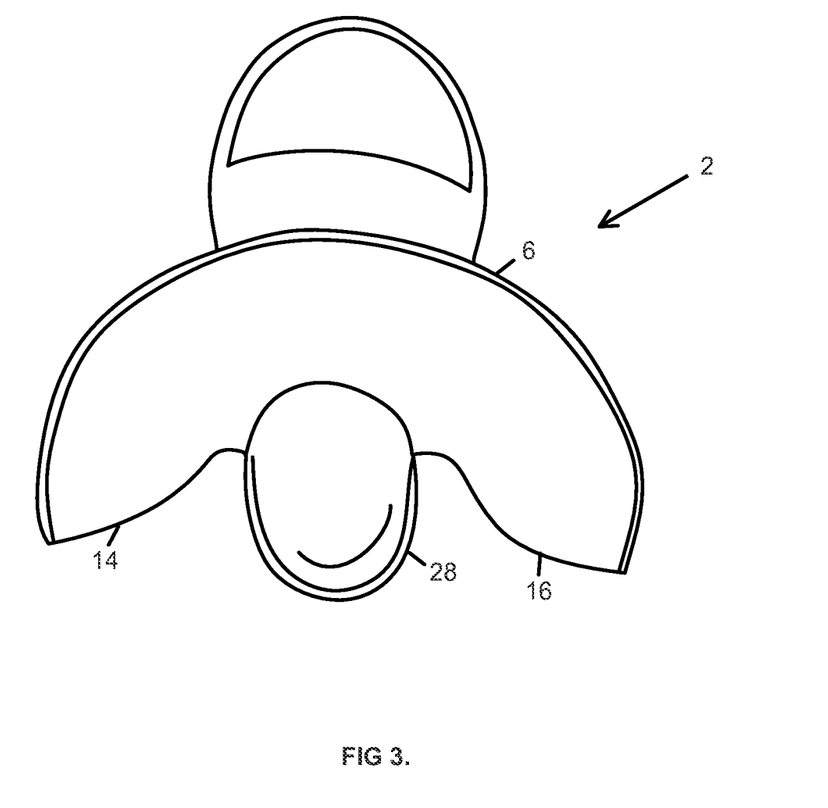
FIG. 3 is a top plan view of one embodiment of the walking boot device in accordance with the present invention.
Figure 4:
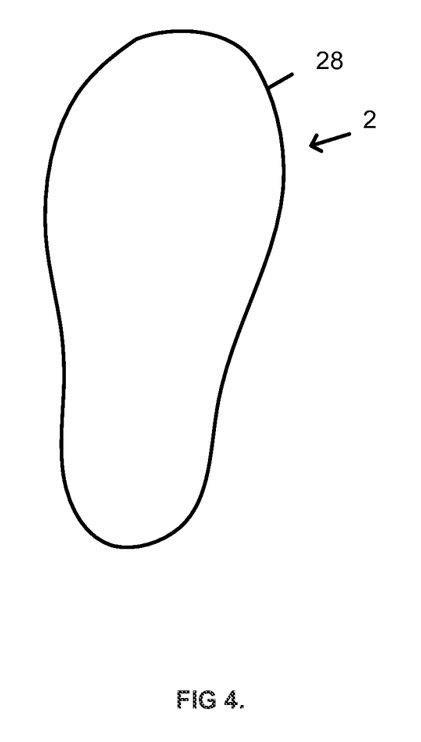
FIG. 4 is a bottom plan view of one embodiment of the walking boot device in accordance with the present invention.
Figure 5:
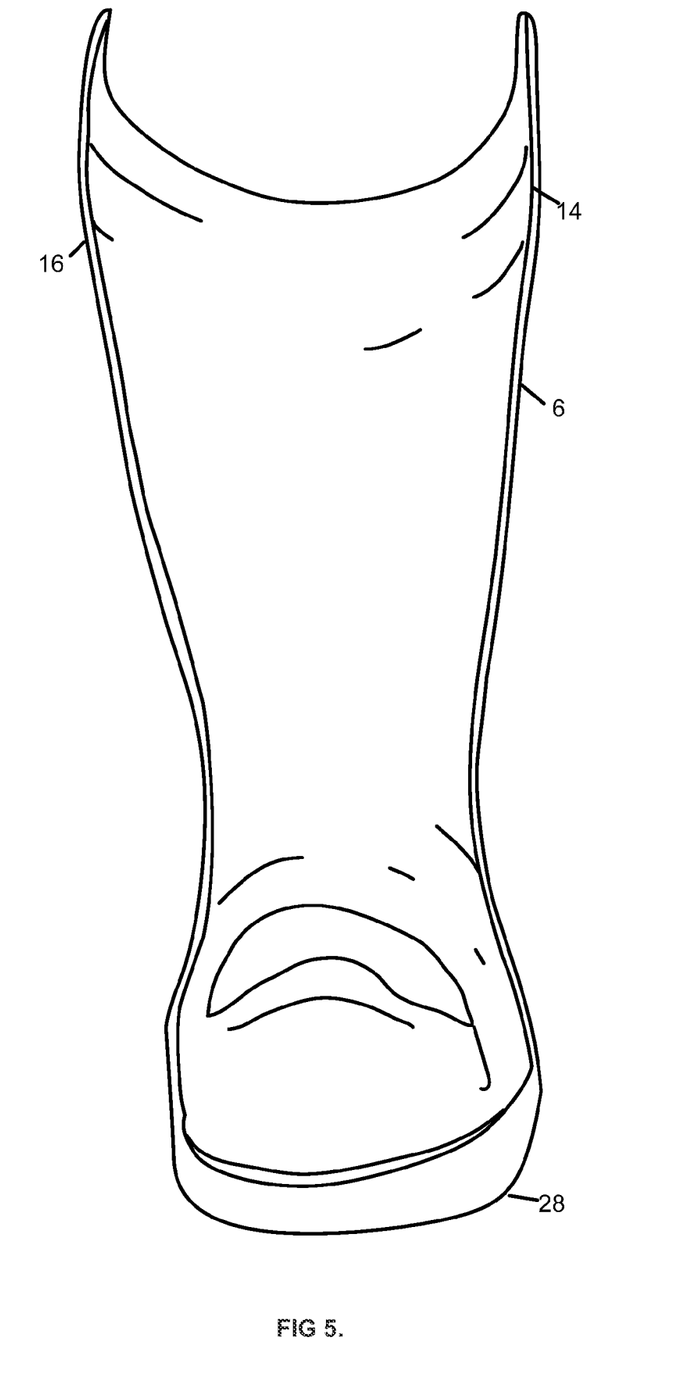
FIG. 5 is a rear view of one embodiment of the walking boot device in accordance with the present invention.
Figure 6:
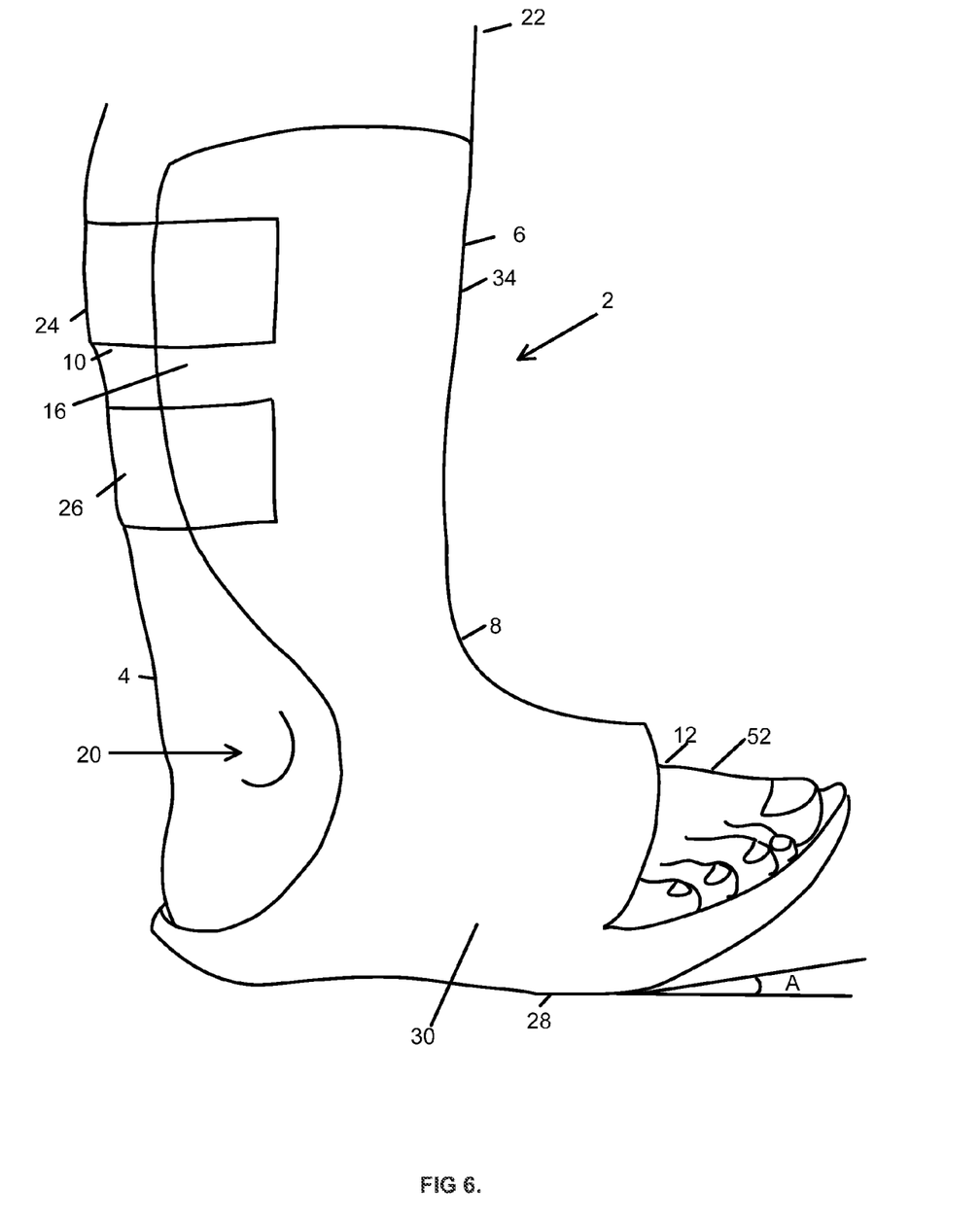
FIG. 6 is a side view of one embodiment of the walking boot device attached to a patient's calf in accordance with the present invention.
Figure 7:
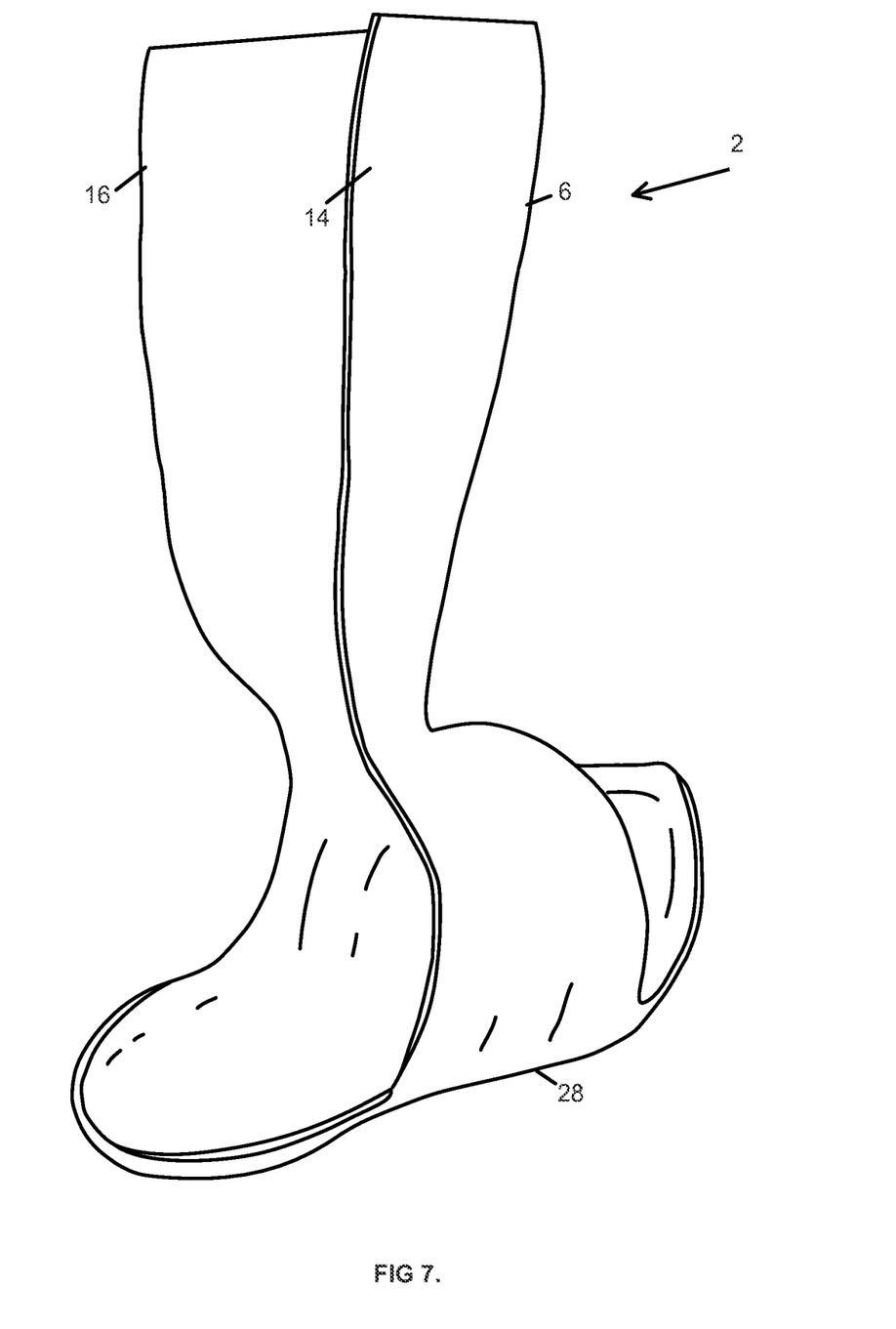
FIG. 7 is an angled view of one embodiment of the walking boot device in accordance with the present invention.

In accordance with the present invention, the post 6 includes medial and lateral wings 14, 16 and defines an area for a medial and lateral malleolus 18, 20, as illustrated in FIG. 6. The post 6 is also narrow at the ankle 4 and wider at the calf 10 for a more anatomical fit, as illustrated in FIGS. 1, 2, and 5-7. As illustrated in FIGS. 2 and 6, some embodiments of the present invention can be secured to a leg 22 using hook and loop fastener (Velcro®) strapping 24, 26 attached to the medial and lateral wings 14, 16 through brackets (not shown) that are riveted into the wings 14, 16. The hook and loop fastener (Velcro®) strapping 24, 26 can be attached to the bracket (not shown) of the lateral wing 16 or medial wing 14 permanently and can be wrapped proximally around the calf 10 posteriorly, away from any bony prominences, by looping the strapping 24, 26 through the bracket (not shown) of the medial wing 14 or lateral wing 16 and fastening the strapping 24, 26 to itself.

In one embodiment, the brackets (not shown) are made of metal. In another embodiment, the brackets (not shown) are made of plastic.

In some embodiments, the device 2 includes a sole 28 that is flat with a predetermined angle A of dorsiflexion at a metatarsal-phalangeal joint 52. In some embodiments, the angle A is about 15°. However, angle A can have other dimensions that are greater than or less than about 15°. In some embodiments, the sole 28 is made of rubber.

Figure 8:
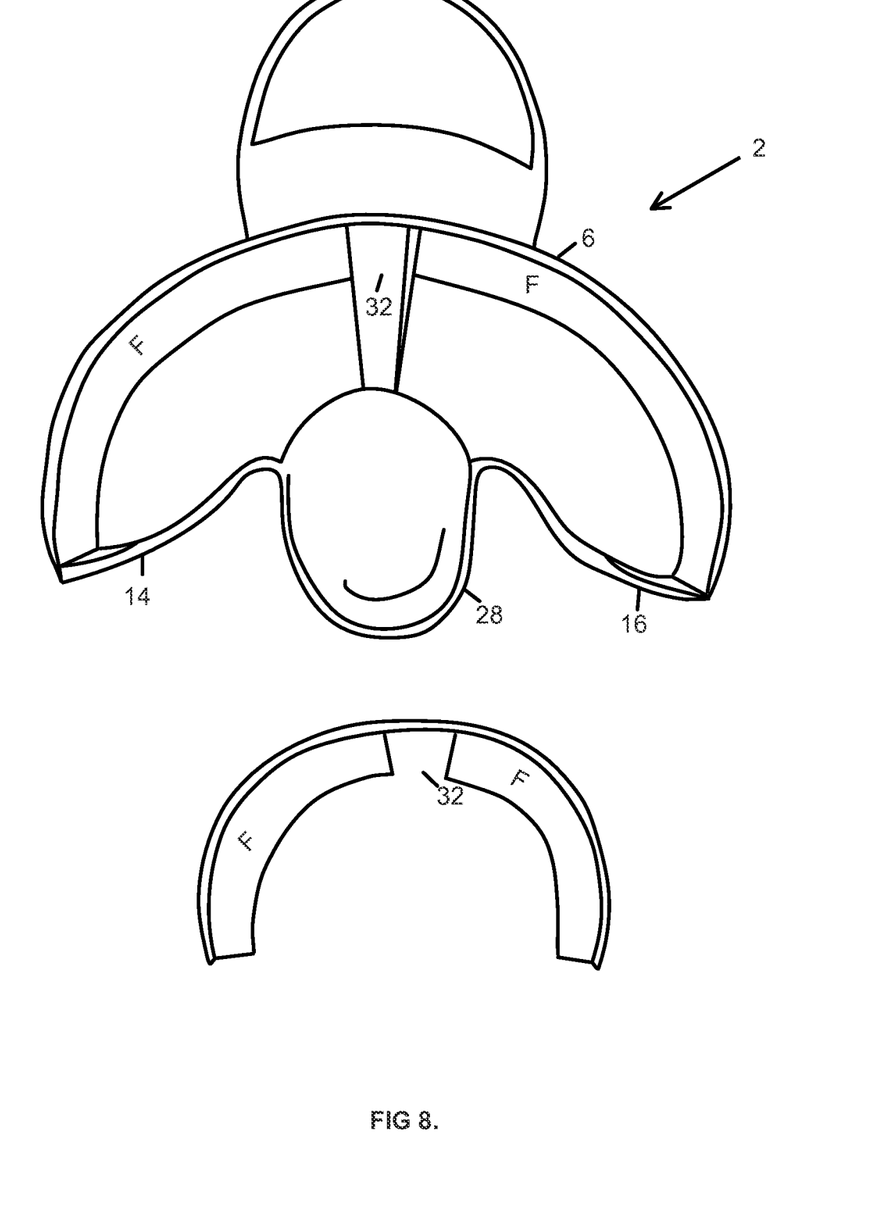
FIG. 8 is a top plan view of one embodiment of the walking boot device with foam interior padding in accordance with the present invention.

In accordance with the present invention, the device 2 can be made of a lightweight plastic that is flexible around the calf 10 proximally and more rigid anteriorly at the forefoot 12 and a foot plate 30. As illustrated in FIG. 8, the device 2 can also include foam F as interior padding all along the post 6 except for an area 32 above an anterior shin 34, which is not lined with foam F.

Figure 9:
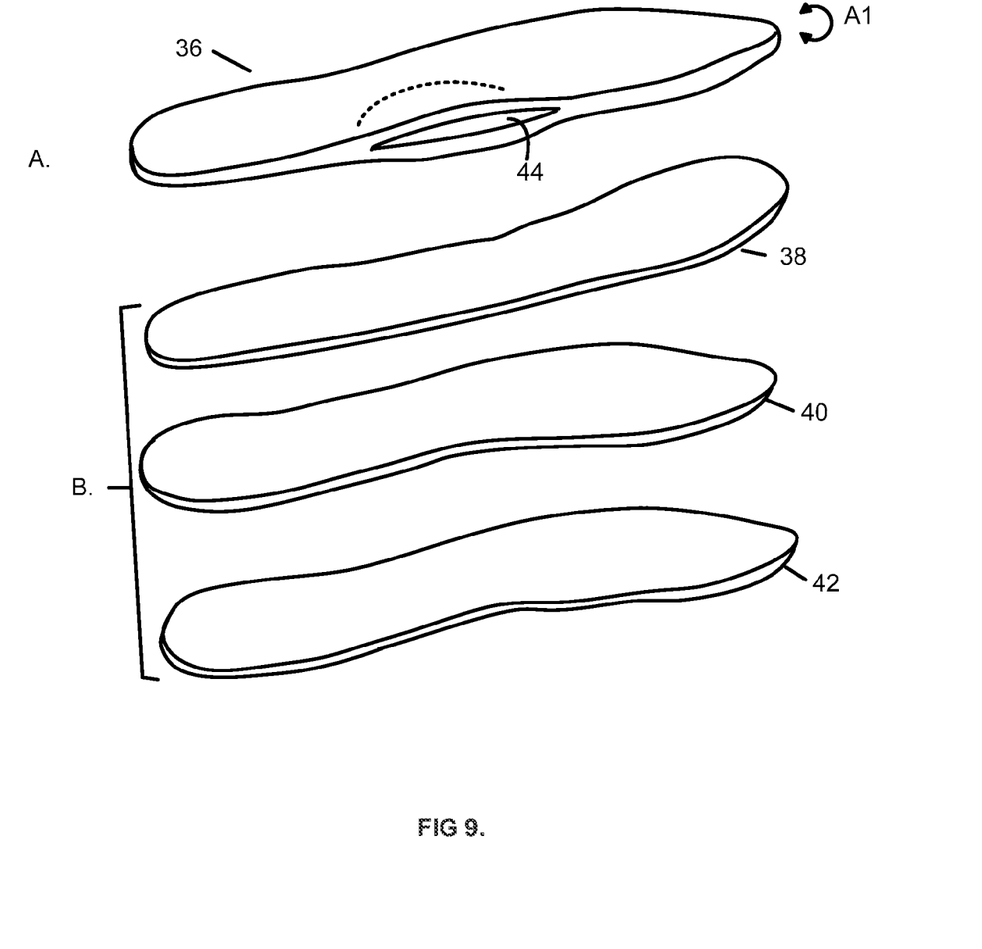
FIG. 9 is a side elevation view of inserts of varying thickness in accordance with the present invention.
Figure 10:
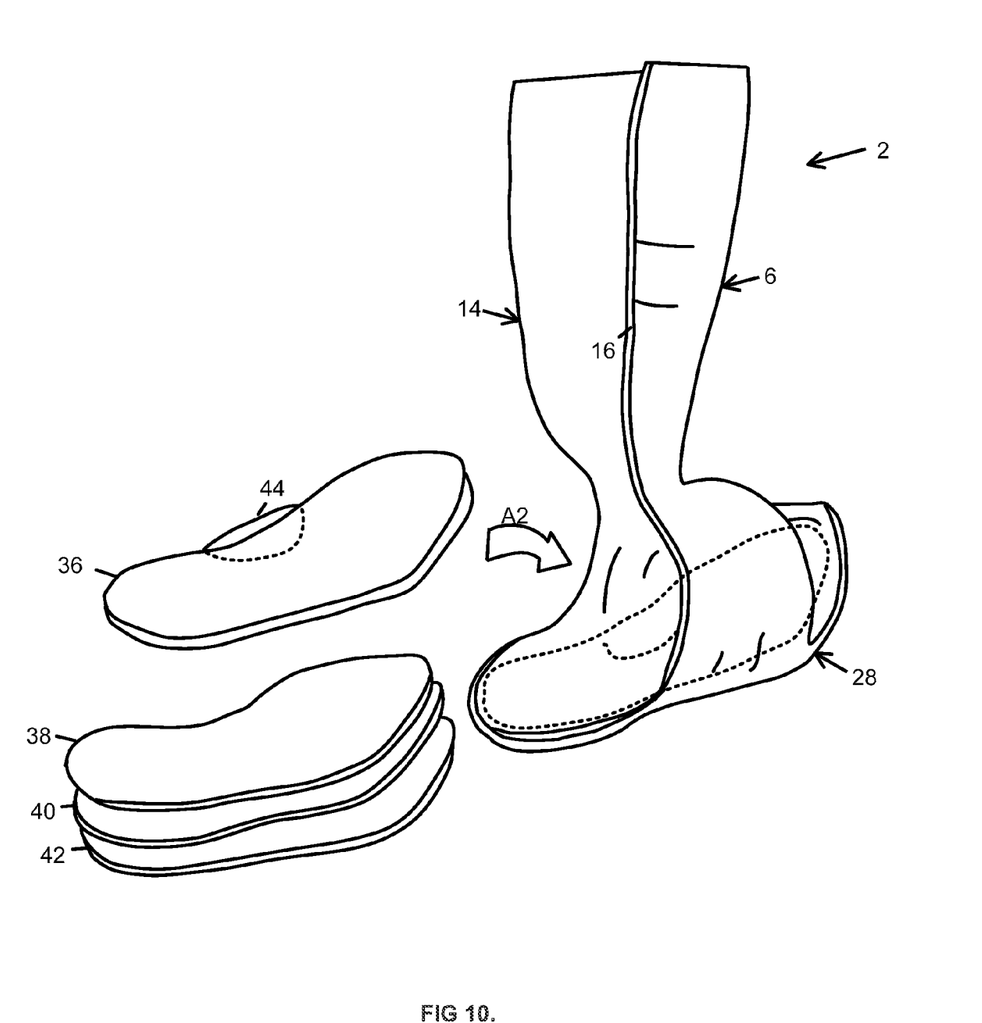
FIG. 10 is a side elevation view of the inserts being inserted into the walking boot device in accordance with the present invention.

In accordance with the present invention, the device 2 can be low-profile and have inserts of varying thickness 36-42, as illustrated in FIGS. 9 and 10. The inserts 36-42 can be made of foam. The inserts 36-42 can be used to accommodate for height inequality of opposing shoe gear by placing them inside the device, as indicated by arrow A2. In some embodiments, the device 2 includes a thick insert 36 which is about 10 mm thick and may include an additional approximate 5 mm of thickness in a medial longitudinal arch 44, thereby making the arch 44 have a thickness of about 15 mm. The device 2 can also include a set of three thinner inserts 38-42 that are about 2 mm thick, which can be used for additional height under the thick insert 36 as needed to accommodate for the height of opposing shoe gear. However, the inserts 36-42 can have other dimensions that are greater than or less than about 2 mm and 10 mm. The thick insert can be reversible, as indicated by arrow A1, to create the arch 44 medially for a right or left foot.

Figure 11:
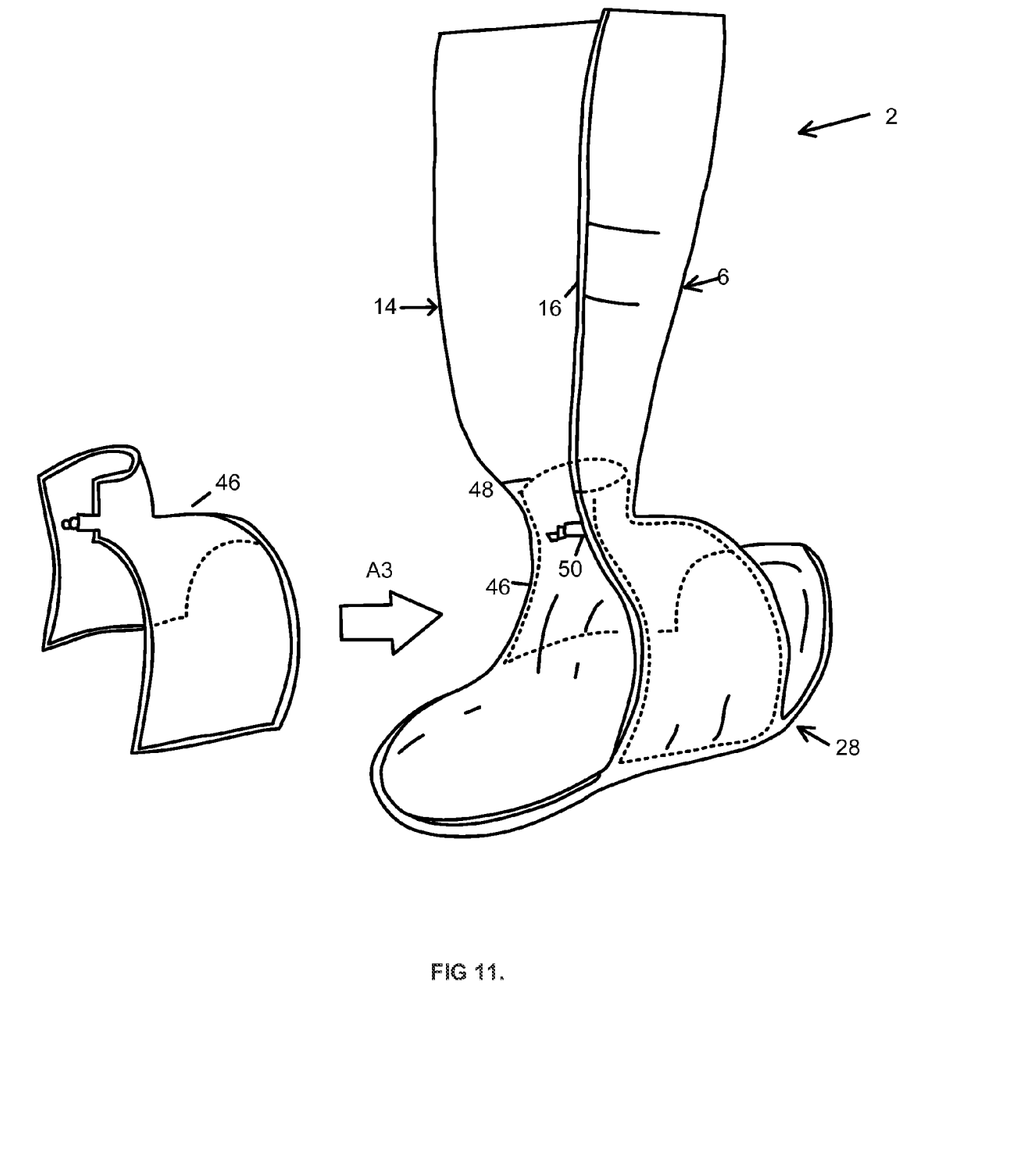
FIG. 11 is a side elevation view of a pneumatic bladder being attached inside the walking boot device in accordance with the present invention.

In some embodiments, the device 2 includes a pneumatic bladder 46 attached to the device in the area around the forefoot 12 dorsally, as indicated by arrow A3 in FIG. 11. The bladder 46 is held in place with hook and loop fastener (Velcro®) strapping 48. The bladder 46 includes a stem 50 as a means to inflate the bladder. The stem 50 may exit the bladder 46 posteriorly above the medial or lateral malleolus 18, 20. In some embodiments, the bladder 46 is made of rubberized plastic.

While the present invention has been described with respect to particular embodiments thereof, it is apparent that numerous other forms and modifications of the invention will be obvious to those skilled in the art. The appended claims and the present invention generally should be construed to cover all such obvious forms and modifications which are within the true spirit and scope of the present invention.

What is claimed is:

1. A walking boot device comprising:
    a single anterior post that is angled at about 90° at an ankle joint from a lateral view, and encompasses an anterior one half of a calf proximally, and a dorsal one half of a forefoot distally;
    hook and loop fastener strapping attached proximally around the calf posteriorly, away from any bony prominences;
    wherein the post includes medial and lateral wings;
    the post defines an area for a medial and lateral malleolus; and
    the post curves more narrowly at the ankle and more widely at the calf,
    wherein the device is made of a lightweight plastic that is flexible around the calf proximally and more rigid anteriorly at the forefoot and a foot plate.

2. The device of claim 1, wherein the device is low-profile.

3. The device of claim 2 further comprising inserts of varying thickness.

4. The device of claim 1 further comprising inserts of varying thickness.

5. The device of claim 4 wherein the inserts are made of foam.

6. The device of claim 4 wherein an insert is about 10 mm thick and includes an additional 5 mm of thickness in a medial longitudinal arch, thereby making the arch about 15 mm thick.

7. The device of claim 6 wherein the insert is reversible.

8. The device of claim 4 further comprising a set of three inserts that are about 2 mm thick.

9. The device of claim 1 further comprising a pneumatic bladder around the forefoot dorsally.

10. The device of claim 9 further comprising inserts of varying thickness.

11. The device of claim 9 wherein the pneumatic bladder is made of rubberized plastic.

12. The device of claim 1 further comprising a sole that is flat with a predetermined angle of dorsiflexion at a metatarsal-phalangeal joint.

13. The device of claim 12 wherein the predetermined angle is about 15°.

14. The device of claim 1 wherein the hook and loop fastener strapping is attached to the medial and lateral wings through brackets that are riveted into the wings.

15. The device of claim 14 wherein the hook and loop fastener strapping is attached to the bracket of the lateral wing or medial wing permanently.

16. The device of claim 14 wherein the brackets are made of metal.

17. The device of claim 14 wherein the brackets are made of plastic.

18. The device of claim 1 further comprising foam as interior padding all along the post except for an area above an anterior shin.

\* \* \* \* \*